United States Patent
Holerca et al.

(10) Patent No.: US 9,592,182 B2
(45) Date of Patent: Mar. 14, 2017

(54) CLEANSING COMPOSITION WITH WHIPPED TEXTURE

(75) Inventors: Marian Holerca, Somerset, NJ (US); Rabab Ahmed, Somerset, NJ (US); Donna Ann Hartnett, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/233,327

(22) PCT Filed: Jul. 20, 2011

(86) PCT No.: PCT/US2011/044649
§ 371 (c)(1),
(2), (4) Date: Jan. 16, 2014

(87) PCT Pub. No.: WO2013/012420
PCT Pub. Date: Jan. 24, 2013

(65) Prior Publication Data
US 2014/0162926 A1  Jun. 12, 2014

(51) Int. Cl.
*A61K 8/04* (2006.01)
*A61Q 19/10* (2006.01)
*A61K 8/36* (2006.01)
*A61K 8/19* (2006.01)

(52) U.S. Cl.
CPC .............. *A61K 8/046* (2013.01); *A61K 8/04* (2013.01); *A61K 8/19* (2013.01); *A61K 8/361* (2013.01); *A61Q 19/10* (2013.01)

(58) Field of Classification Search
CPC .................................. C11D 1/79; A61K 8/046
USPC .................................................. 510/159, 238
See application file for complete search history.

(56) References Cited

U.S. PATENT DOCUMENTS

| | | | | |
|---|---|---|---|---|
| 3,926,827 A * | 12/1975 | Mangeli | ............. | C11D 11/0082 510/356 |
| 4,915,938 A * | 4/1990 | Zawadzki | ................ | 424/70.122 |
| 4,992,263 A | 2/1991 | Tesmann et al. | | |
| 5,147,574 A | 9/1992 | MacGilp et al. | | |
| 5,246,613 A | 9/1993 | Gilbert et al. | | |
| 5,439,615 A * | 8/1995 | Lefebvre et al. | ............. | 510/433 |
| 5,500,152 A | 3/1996 | Helliwell | | |
| 5,637,758 A * | 6/1997 | Sajic et al. | ..................... | 560/147 |
| 5,688,978 A * | 11/1997 | Lefebvre et al. | ............... | 554/69 |
| 5,834,413 A * | 11/1998 | Durbut et al. | ................ | 510/365 |
| 5,962,396 A * | 10/1999 | Pollack et al. | ................ | 510/433 |
| 5,994,280 A * | 11/1999 | Giret et al. | .................. | 510/130 |
| 6,180,582 B1 * | 1/2001 | Durbut et al. | ................ | 510/365 |
| 6,284,230 B1 * | 9/2001 | Sako et al. | .................. | 424/70.11 |
| 6,368,582 B1 * | 4/2002 | Mitsumatsu | ................ | 424/70.11 |
| 6,511,955 B1 * | 1/2003 | Drapier et al. | ................ | 510/421 |
| 6,533,873 B1 * | 3/2003 | Margosiak | ......... | C11D 17/0013 134/39 |
| 6,562,773 B1 * | 5/2003 | Drapier et al. | ................ | 510/238 |
| 6,608,013 B1 * | 8/2003 | Drapier et al. | ................ | 510/238 |
| 6,767,878 B1 | 7/2004 | Paye et al. | | |
| 2003/0050200 A1 | 3/2003 | Chen | | |
| 2003/0083210 A1 | 5/2003 | Goldberg et al. | | |
| 2003/0180242 A1 * | 9/2003 | Eccard et al. | ............. | 424/70.11 |
| 2005/0043194 A1 | 2/2005 | Macaulay et al. | | |
| 2005/0136026 A1 | 6/2005 | Qiu et al. | | |
| 2006/0035807 A1 * | 2/2006 | Kasturi et al. | ................ | 510/475 |
| 2006/0135397 A1 | 6/2006 | Bissey-Beugras et al. | | |
| 2007/0032393 A1 | 2/2007 | Patel et al. | | |
| 2007/0179078 A1 | 8/2007 | Collin et al. | | |
| 2007/0199138 A1 * | 8/2007 | Zhurin | ..................... | E03D 3/00 4/300 |
| 2007/0287648 A1 | 12/2007 | Moaddel et al. | | |
| 2008/0108714 A1 | 5/2008 | Swazey et al. | | |
| 2009/0156450 A1 | 6/2009 | Tsaur | | |
| 2010/0062961 A1 | 3/2010 | Post et al. | | |
| 2010/0075881 A1 | 3/2010 | Tsaur | | |
| 2011/0000500 A1 | 1/2011 | Luna | | |
| 2014/0162926 A1 * | 6/2014 | Holerca et al. | ............... | 510/159 |

FOREIGN PATENT DOCUMENTS

| | | |
|---|---|---|
| CA | 2211313 | 2/1998 |
| CA | 2534923 | 2/2005 |
| DE | 10102009 | 8/2002 |
| EP | 1500385 | 1/2005 |
| EP | 1718268 | 11/2006 |
| FR | 2837697 | 10/2003 |
| FR | 2850017 | 7/2004 |
| FR | 2850017 A1 * | 7/2004 |
| JP | 2011-105787 | 6/2011 |
| RU | 2254119 | 6/2005 |
| WO | WO 03/037294 | 5/2003 |
| WO | WO 03/039493 | 5/2003 |
| WO | WO 2007102972 A1 * | 9/2007 |

OTHER PUBLICATIONS

International Search Report and Written Opinion for International Application No. PCT/US2011/044649 mailed on May 7, 2012.

* cited by examiner

*Primary Examiner* — Mark Eashoo
*Assistant Examiner* — M. Reza Asdjodi

(57) ABSTRACT

A liquid cleansing composition comprising water in a sufficient amount to form a fluid composition; fatty acid soap; a divalent metal salt in an amount to provide a viscosity to entrain gas; and entrained gas to provide a specific gravity of not greater than 1.05 g/cm3. Optionally, a surfactant can also be included. The cleansing composition has a whipped texture. Also, a method of making the liquid cleansing composition.

13 Claims, No Drawings

CLEANSING COMPOSITION WITH WHIPPED TEXTURE

FIELD OF THE INVENTION

Disclosed are cleansing compositions that have a whipped texture.

BACKGROUND OF THE INVENTION

While surfactant containing compositions can be structured so that air can be entrained into the composition to form a creamy texture, it is a continuing desire to provide new aesthetics to these compositions.

It would be desirable to provide a structured, liquid soap composition that has a whipped texture to provide a new aesthetic.

BRIEF SUMMARY OF THE INVENTION

A liquid cleansing composition comprising water in a sufficient amount to form a fluid composition; fatty acid soap; a divalent metal salt in an amount to provide a viscosity to entrain gas; and entrained gas to provide a specific gravity of not greater than 1.05 g/cm$^3$. Optionally, a surfactant can also be included.

Also, a method comprising applying the composition to skin and cleansing the skin, and optionally, rinsing the skin.

Also, a method of making a whipped cleansing composition comprising: providing a base comprising water in an amount of 55 to 70% by weight of the base composition, and fatty acid soap; mixing the base with a water and a divalent metal salt, wherein a weight ratio of base composition to water is 50:50 to 75:25 or 60:40 to 70:30, and wherein the amount of salt is sufficient to provide a viscosity to entrain gas; and entraining a gas to provide a specific gravity of not greater than 1.05 g/cm$^3$. Optionally, the base also includes a surfactant.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

Disclosed is a liquid cleansing composition comprising water in an amount sufficient to form a fluid composition, a fatty acid soap, a divalent metal salt in an amount to provide a viscosity of 3000 to 65000 mPas, and entrained gas. Optionally, a surfactant can also be included. When soap and surfactant are both present, the composition is a soap mix.

The structured soap composition provides a unique aesthetic. When surfactant only compositions are structured and air is entrained, the composition has a creamy appearance. The composition allows visible sized bubbles to remain in the composition to provide a whipped appearance. The visual difference is similar to cream (for surfactant only) versus whipped cream (for soap). In another analogy, the difference is similar to soft serve ice cream (for surfactant only) versus Italian ice (for soap). By viewable it is meant that at least a portion of the entrained gas can be seen by a person with an unaided eye at 20/20 or corrected to 20/20 with glasses or contact lenses at a distance of 30 cm from the composition under incandescent light, florescent light, or sunlight.

In certain embodiments, the composition can provide a specific gravity of less than 1 g/cm$^3$, or less than 0.99 g/cm$^3$. In one embodiment, the specific gravity is 0.98 g/cm$^3$. In one embodiment, the specific gravity is 0.8 to 1.05 g/cm$^3$.

The fatty acid soap can be any of the neutralized fatty acids. Typical fatty acids used for soaps include, myristic acid, lauric acid, palmitic acid, stearic acids, and other fatty acids. Sources of fatty acids include coconut oil, palm oil, palm kernel oil, tallow, avocado, canola, corn, cottonseed, olive, hi-oleic sunflower, mid-oleic sunflower, sunflower, palm stearin, palm kernel olein, safflower, and babassu oils. The fatty acids can be neutralized with any neutralizing agent, such as a base, to form a soap. Typical bases include, but are not limited to, sodium hydroxide, potassium hydroxide, and triethanolamine. In one embodiment, the soap is a potassium soap. In certain embodiments, the fatty acid soap is present in the composition in an amount up to 30 weight %. In other embodiments, the amount is 10 to 30 weight %, 10 to 20 weight %, or at least 11, 12, 13, 14, 15, 16, 17, 18, 19, or 20 up to 30 weight %.

The soap can be made in situ in the composition by mixing fatty acids with the neutralizing agent. In certain embodiments, the molar amount of fatty acids is greater than the molar amount of neutralizing agent such that fatty acid remains in the composition. In certain embodiments, the total amount of soap includes the neutralized fatty acids and free fatty acids. In certain embodiments, the amount of free fatty acids is up to 20 weight % of the total amount of soap in the composition.

The composition optionally includes a surfactant. The surfactant is a non-soap surfactant, which is in addition to the fatty acid soap that is in the composition. The surfactant can be any anionic, nonionic, amphoteric, or zwitterionic surfactant, or combinations thereof. The amount of surfactant in the composition is at least 1 weight %. In other embodiments, the amount is 1 to 20 weight %, or at least 2, 3, 4, 5, 6, 7, 8, 9, or 10 weight %.

A variety of anionic surfactants can be utilized in the composition including, for example, long chain alkyl ($C_6$-$C_{22}$) materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI), long chain alkyl glyceryl ether sulfonates (AGES), sulfosuccinates and the like. These anionic surfactants can be alkoxylated, for example, ethoxylated, although alkoxylation is not required. These surfactants are typically highly water soluble as their sodium, potassium, alkyl and ammonium or alkanol ammonium containing salt form and can provide high foaming cleansing power. Other equivalent anionic surfactants may be used. In one embodiment, the anionic surfactant comprises sodium laureth sulfate, sodium pareth sulfate, and combinations thereof. Anionic surfactants can be included in any desired amount. In one embodiment, anionic surfactants are present in the composition in an amount of 0 to about 15% by weight.

Amphoteric surfactants may also be included in the composition. These surfactants are typically characterized by a combination of high surfactant activity, lather forming and mildness. Amphoteric surfactants include, but are not limited to, derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to, a range of betaines including, for example, high alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups such as the cocamidopropyl and cocoamidoethyl betaines. Amphoteric surfactants can be included in any desired amount. In one embodiment, amphoteric surfactants are present in the composition in an amount of 0 to about 15% by weight.

Examples of nonionic surfactants include, but are not limited to, polysorbate 20, long chain alkyl glucosides having $C_8$-$C_{22}$ alkyl groups; coconut fatty acid monoethanolamides such as cocamide MEA; coconut fatty acid diethanolamides, fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (for example the PLURONIC™ block copolymers commercially available from BASF); fatty acid alkylolamides, (fatty acid amide polyethylene glycols); N-alkyl-, N-alkoxypolyhydroxy fatty acid amides; sucrose esters; sorbitol esters; polyglycol ethers; and combinations thereof. Nonionic surfactants can be included in any desired amount.

In one embodiment, the surfactant is an alkyl polyglucoside (APG) surfactant. Examples of APG surfactants include, but are not limited to, decyl glucoside and coco glucoside.

A divalent metal salt is included in the composition. In certain embodiments, it can be included in an amount such that the composition has a viscosity of 3000 to 65000 mPas without entrained gas. In certain embodiments, the divalent metal salt is a magnesium salt. In certain embodiments, the magnesium salt can be magnesium chloride, $MgCl_2*6H_2O$, magnesium sulfate, or $MgSO_4*7H_2O$. In certain embodiments, the amount of salt, preferably magnesium, is present in an amount of at least 2 weight %, at least 2.5 weight %, at least 3 weight %, or at least 4 weight % of the composition.

Viscosity is measured using a Brookfield DV-II Viscometer at room temperature (23-25° C.) using Spindle 4 at 20 RPM for 30 sec. Viscosity is measured at 24 hours after making.

Water is present in the composition in an amount that is sufficient to form a fluid composition. In certain embodiments, the amount of water is at least 65 weight %, or 65 to 90 weight %. In other embodiments the amount of water is 75 to 85 weight %.

Gas is entrained into the composition. The amount of gas can be any desired amount to provide a desired texture. The gas can be any gas. In one embodiment, the gas is air. In certain embodiments, the amount of gas is 5 to 15%, 8 to 12%, or about 10%. The amount of gas is based on comparing equal volumes of the weight a composition without gas to the weight of a composition with gas. For example, if the weight of the composition with gas is 90% of the weight of the composition without gas, then the composition with gas has about 10% gas.

In certain embodiments, the composition may include a foam booster to increase the amount of foam. In certain embodiments, the amount of foam booster is 0.1 to 3% by weight of the composition. In other embodiments, the amount is at least 0.2, 0.3, 0.4, 0.5, 0.6, 0.7, 0.8, 0.9, 1, 1.5, 2, or 2.5% by weight up to 3% by weight of the composition. Foam boosters can be any foam booster. Examples of foam boosters include, but are not limited to, fatty acid monoethanol amide, fatty acid diethanol amide, cocomonoethanol amide (CMEA), cocodiethanol amide (CDEA), and lauryl diethanol amide.

In other embodiments, the composition may include any of following materials in any desired amount to achieve a desired effect in the composition (amounts that can be used in some embodiments are provided): one or more alkaline salts, for example, sodium chloride, sodium sulfate, sodium carbonate, sodium bicarbonate and/or their equivalents (0 to 5% by weight); foaming agents, for example decyl glucoside, and/or their equivalents (0 to 3% by weight); glyceryl esters and derivatives, for example glycol distearate, and/or their equivalents (0 to 3%; by weight); sequestrants, for example, tetrasodium EDTA, and/or their equivalents (0 to 2% by weight); biocides, for example, Triclosan (2,4,4'-trichloro-2'-hydroxydiphenyl ether), DMDM hydantoin, formaldehyde and/or imidazolidinyl urea, and/or their equivalents (0 to 2% by weight); organic acids, for example, citric acid and/or formic acid and/or their equivalents (0 to 2% by weight); viscosity modifiers (0 to 2% by weight); fragrances and/or perfumes (0 to 5% by weight); preservatives, for example, phenoxyethanol, formaldehyde solution, parabens, pentanediol or sorbic acid (0 to 2% by weight); pearlizing agents, for example, glycol distearic esters, such as ethylene glycol distearate, but also fatty acid monoglycol esters (0 to 3% by weight); and dyes and pigments that are approved and suitable for cosmetic purposes.

Also, a method comprising applying the composition to skin and cleansing the skin, and optionally, rinsing the skin.

In one embodiment, the composition can be made by a method comprising: providing a base comprising water in an amount of 55 to 70% by weight of the base composition, fatty acid soap, and surfactant; mixing the base with a water and salt, wherein a weight ratio of base composition to water is 50:50 to 75:25 or 60:40 to 70:30, and wherein the amount of salt is sufficient to provide a viscosity of 3000 to 65000 mPas; and entraining a gas.

SPECIFIC EMBODIMENTS

The invention is further described in the following examples. The examples are merely illustrative and do not in any way limit the scope of the invention as described and claimed.

The following base composition is prepared by mixing of the ingredients. The amounts listed are based on the as supplied weights of the materials. The formula is for a clear composition, but an opaque composition can be prepared by removing 2.5 weight % water and adding 2.5 weight % glycol distearate.

| | wt % |
|---|---|
| Demineralized Water | 63.8 |
| 47% Potassium Hydroxide solution | 8.4 |
| Lauric Acid | 8.6 |
| C12-C18 Fatty Acid Blend | 4.2 |
| Myristic Acid | 3.4 |
| Hydroxyethyl Cellulose | 0.46 |
| Glycerin | 2.5 |
| Polyethylene Oxide(Polyox WSR-205)(PEG-14M) | 0.1 |
| Alkyl Polyglucoside surfactant 600 –50% | 5 |
| Cocomonoethanolamide | 3 |
| Minors (pH adjustment) | Q.S. |

The following composition was selected for entraining with gas.

| Ingredient | Weight % |
|---|---|
| Soap-Mix Base* | 57.3 |
| DI Water | 36.7 |
| Hydroxy Ethyl Cellulose | 0.6 |
| Magnesium Salt | 4 |
| Minors (color, fragrance, preservative) | Q.S. |

The materials are mixed together. Under agitation, air is entrained into the composition. About 10% air is added. The resulting composition had a specific gravity of 0.98 g/cm$^3$.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A personal care, liquid cleansing composition comprising:
   a) water in a sufficient amount to form a fluid composition;
   b) fatty acid soap;
   c) a water soluble divalent metal salt in an amount to provide a viscosity to entrain gas, wherein the water soluble divalent metal salt is selected from the group consisting of magnesium chloride, $MgCl_2*6H_2O$, magnesium sulfate, and $MgSO_4*7H_2O$; and
   d) entrained gas to provide a specific gravity of not greater than 1.05 g/cm$^3$,
   wherein the fatty acid soap is present in an amount of at least 21 weight % of the composition,
   wherein the composition contains gas bubbles of a size that are visually observable by naked eye,
   wherein the composition has 5 to 15% gas,
   wherein the composition has a viscosity of 3,000 to 65,000 mPas without entrained gas, and
   wherein the composition is suitable for cleansing skin.

2. The liquid cleansing composition of claim 1 further comprising a surfactant.

3. The liquid cleansing composition of claim 2 wherein the surfactant comprises an alkyl polyglucoside surfactant.

4. The liquid cleansing composition of claim 2, wherein the surfactant is present in an amount of at least 1% by weight of the composition.

5. The liquid cleansing composition of claim 1, wherein the amount of the water soluble divalent metal salt is at least 2 weight % of the composition.

6. The liquid cleansing composition of claim 1, wherein the fatty acid soap comprises lauric acid soap and myristic acid soap.

7. The liquid cleansing composition of claim 1, wherein the fatty acid soap is a potassium soap.

8. The liquid cleansing composition of claim 1, wherein the composition comprises potassium fatty acid soap, alkyl polyglucoside surfactant, glycerin, polyethylene oxide, hydroxyethyl cellulose, and cocomonoethanolamide.

9. The liquid cleansing composition of claim 1, wherein the composition has a specific gravity less than 1 g/cm$^3$.

10. The liquid cleansing composition of claim 1, wherein the composition has 8 to 12% gas.

11. The liquid cleansing composition of claim 1 further comprising a foam booster, optionally in an amount of 0.1 to 3% by weight of the composition.

12. The liquid cleansing composition of claim 11, wherein the foam booster is at least one foam booster chosen from fatty acid monoethanol amide, fatty acid diethanol amide, cocomonoethanol amide (CMEA), cocodiethanol amide (CDEA), and lauryl diethanol amide.

13. A method comprising applying the composition of claim 1 to skin and cleansing the skin, and optionally, rinsing the skin.

* * * * *